US00PP10028P

United States Patent [19]

Rother

[11] Patent Number: Plant 10,028

[45] Date of Patent: Sep. 16, 1997

54] PETUNIA PLANT NAMED 'SUNWINE'

76] Inventor: Reinhard W. Rother, 56 Emerald Monbulk Road, Emerald, Victoria 3782, Australia 21] Appl. No.: 679,895

22] Filed: Jul. 15, 1996

51] Int. Cl.[6] ..... A01H 5/00

52] U.S. Cl. ..... Plt./68.1

58] Field of Search ..... Plt./68.1

*Primary Examiner*—James R. Feyrer
*Attorney, Agent, or Firm*—C. A. Whealy

[57] ABSTRACT

A distinct cultivar of Petunia plant named 'Sunwine', characterized by its unique dark red purple flowers; vigorous growth habit and rapid growth rate; decumbent and spreading plant habit; freely branching habit; early flowering; very floriferous with numerous flowers per plant; and tolerant to rain, drought and temperature extremes.

2 Drawing Sheets

1

The present invention relates to a new and distinct cultivar of Petunia plant, botanically known as *Petunia axillaris*, and hereinafter referred to by the cultivar name Sunwine.

The new cultivar is a product of a planned breeding program conducted by the inventor in Emerald, Victoria, Australia. The objective of the breeding program was to create new Petunia cultivars having large flowers, a spreading plant habit, and desirable flower colors.

The new cultivar originated from a cross made by the inventor of two unidentified proprietary Petunia selections.

The cultivar Sunwine was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar Sunwine has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Sunwine'. These characteristics in combination distinguish 'Sunwine' as a new and distinct cultivar:

1. Unique dark red purple flowers.
2. Vigorous growth habit and rapid growth rate.
3. Decumbent and spreading plant habit.
4. Freely branching habit. Plants do not require pinching.
5. Early flowering.
6. Very floriferous with numerous flowers per plant.
7. Tolerant to rain, drought and temperature extremes.

The accompanying colored photographs illustrate the overall appearance of the new cultivar, showing the colors as true as it is reasonably possible to obtain in colored reproductions of this type.

The first photograph comprises a side perspective view of a typical plant of the cultivar Sunwine.

The second photograph comprises a close-up view of individual flowers of the cultivar Sunwine. Flower and foliage colors may appear different than the actual colors due to light reflectance.

In the following description, color references are made to The Royal Horticultural Society Colour Chart except where general terms of ordinary dictionary significance are used. Measurements are averages from ten specimens selected at random from five plants.

Botanical classification: *Petunia axillaris* cultivar Sunwine.

2

Parentage:

*Male or pollen parent.*—*Petunia axillaris*, inventor's unidentified proprietary selection.

*Female or seed parent.*—*Petunia axillaris*, inventor's unidentified proprietary selection.

Propagation:

*Type cutting.*—Terminal vegetative cuttings.

*Time to initiate roots.*—About ten days at 21C soil temperature.

*Rooting habit.*—Numerous, fine, fibrous, and well-branched.

Plant Description:

*Form.*—Indeterminate, decumbent, diffuse spreading, viscid, glandular pubescent.

*Branching habit.*—Freely branching.

*Plant height.*—About 10.5 cm.

*Plant width.*—About 3cm.

*Vigor.*—Vigorous.

*Crop time.*—Eight to nine weeks from a unrooted cutting to a 10.5-cm finished and flowering container.

*Foliage description.*—Leaves simple, generally symmetrical, sessile, and long persisting. Letters at first whorled, later alternate, somewhat fleshy. Size (largest leaves): Length: About 10.5 cm. Width: About 3 cm. Thickness: About 2 mm. Shape: Elliptic. Aspect: Horizontal to upright. Apex: Acute. Base: Attenuate. Margin: Entire. Texture: Pubescent. Color: Young foliage upper side: 137A. Young foliage under side: 147B. Mature foliage upper side: 137A. Mature foliage under side: 147B.

*Stem description.*—Stems upright to spreading, hirsute. Stem diameter: About 4 cm. Internode length: About 2.7 cm. Stem color: 144A with red, 79A, areas at nodes.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 6.5 cm. Height: About 5 cm. Flower tube width at distal end: About 1.6 cm. Petal quantity: Five, fused. Petal apex: Acuminate to obtuse. Margin: Entire. Texture: Pubescent on outside, smooth and velvety on inside. Color: Flower throat (inside): 77A. Flower throat vein color (inside): 79A. Flower tube color (outside): 83A.

Flower tube vein color (outside): 79A. Petal color, inside: Darker and more red than 80A. Petal vein color, inside: 79A. Petal color, outside: 77A. Petal vein color, outside: 79A.

*Sepals.*—Quantity: Five. Size: Length: About 2 cm. Width: About 6 mm. Shape: Elliptic. Apex: Obtuse. Margin: Entire. Texture: Pubescent Aspect: Upright to horizontal. Color: Inside: 137A. Outside: Immature: 79A. Mature: 137B.

*Pedicel.*—Aspect: Upright. Size: Length: About 1.8 cm. Width: About 2 mm. Texture: Pubescent. Color: 144A with dark purple, 83A, areas.

*Reproductive organs.*—Stigma below anthers, superior ovary. Stamens: Stamen number: Five, four are didymous. Anther color: Blue. Filament color: Blue. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

It is claimed:

1. A new and distinct cultivar of Petunia plant named 'Sunwine', as illustrated and described.

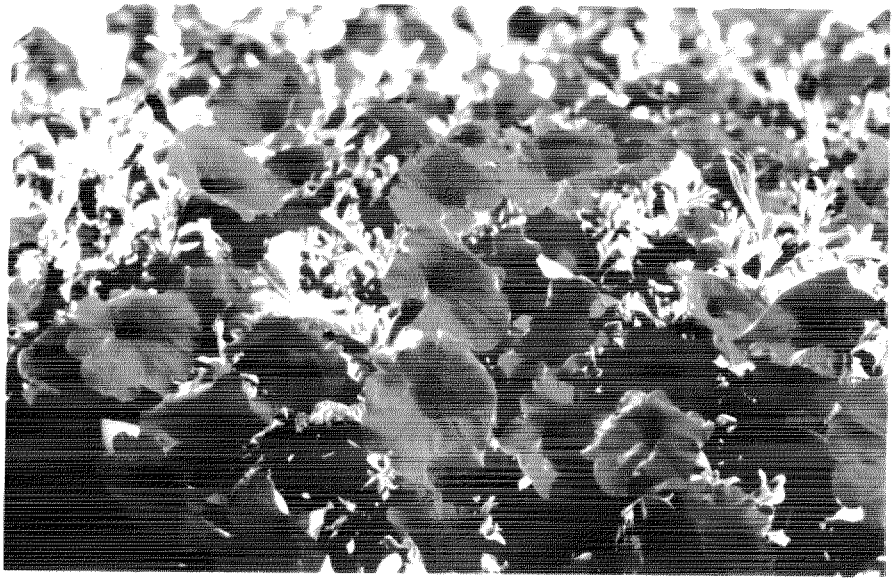

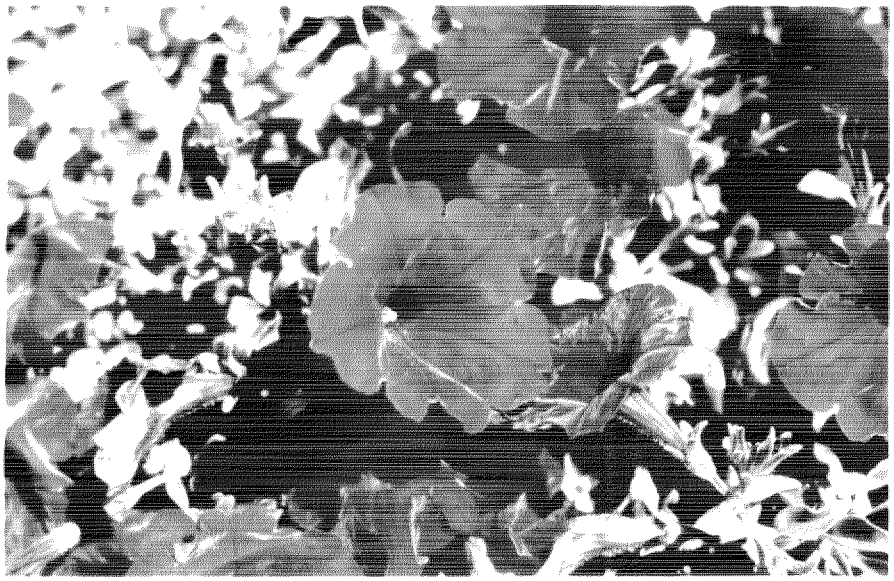

* * * * *